United States Patent [19]

Woodcock

[11] 3,959,171

[45] May 25, 1976

[54] OPTICAL FILTER FOR NEODYMIUM LASER LIGHT

[75] Inventor: Richard Forrest Woodcock, South Woodstock, Conn.

[73] Assignee: American Optical Corporation, Southbridge, Mass.

[22] Filed: Aug. 1, 1974

[21] Appl. No.: 493,588

[52] U.S. Cl............................. 252/300; 106/47 R; 106/54; 428/428
[51] Int. Cl.².......................................... G02B 5/22
[58] Field of Search....... 252/300, 301.4 F, 301.4 P; 106/54, 47 R; 428/428

[56] References Cited
UNITED STATES PATENTS

| | | |
|---|---|---|
| 2,805,166 | 9/1957 | Loffler.................................. 106/54 |
| 3,081,178 | 3/1963 | Weissenberg et al............. 106/47 Q |
| 3,703,388 | 11/1972 | Araujo et al...................... 106/47 R |
| 3,726,698 | 4/1973 | Hares et al........................... 252/300 |

*Primary Examiner*—Benjamin R. Padgett
*Assistant Examiner*—Deborah L. Kyle
*Attorney, Agent, or Firm*—H. R. Berkenstock, Jr.; William C. Nealon

[57] ABSTRACT

An optical filter includes glass doped with erbium ($Er^{3+}$) ions for absorbing light at about 530 nm for protection against frequency doubled Nd-laser light; and to provide protection against Nd-laser light, ferrous ($Fe^{2+}$) ions are included in the glass. The glass base may be changed to broaden the absorption band, increase the absorption coefficient, or to shift the absorption band towards longer wavelengths.

5 Claims, 1 Drawing Figure

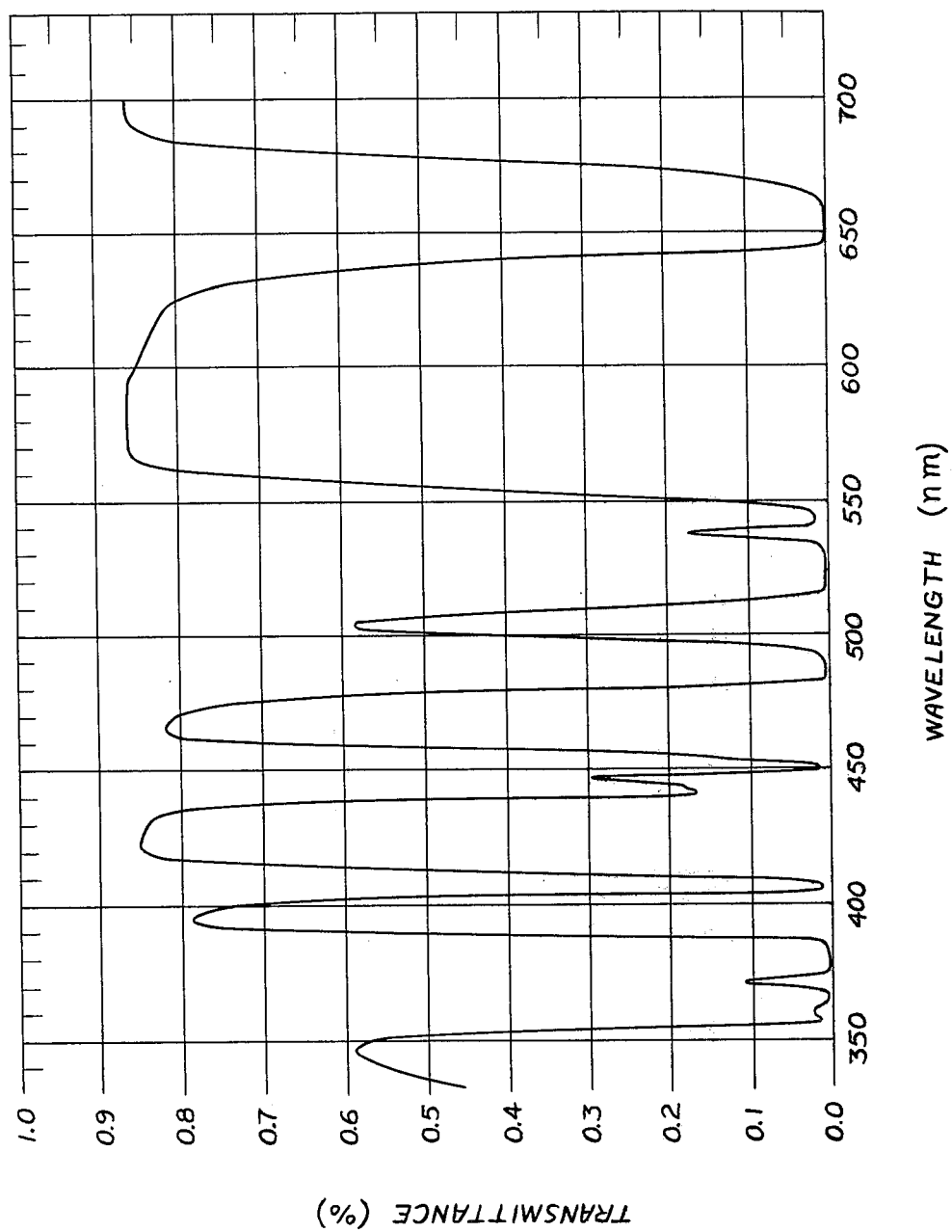

OPTICAL FILTER FOR NEODYMIUM LASER LIGHT

A laser light beam is a very high energy light source, and a substantial amount of laser light is in the near infrared or infrared wavelength ranges. This high energy radiation poses a health hazard, and particularly the eyes of the workers require protection from the radiation of a laser light. Various filters, in the form of eyeglasses, face shields, goggles or the like, have been suggested to provide protection from such high energy radiation. The known filters are, however, in the form of thin films of synthetic plastics having a compound which provides elemental copper or a copper cation absorbed on the surface of the plastic. One such film is described in U.S. Pat. No. 2,861,896, where finely divided particles of elemental copper are dispersed in the thin film. The elemental copper particles provide the filtering function, which is based on a scattering of the light. The film described in U.S. Pat. No. 2,816,047 absorbs an organic dye on the surface of a thin, preformed film, and the film must be used by securing it to a glass lens or the like. One example given provides that a polyvinyl acetate film is dipped in an aqueous aniline solution and is dried. The film is then dipped in an aqueous solution of an oxidizing agent, which may be a soluble copper salt. The dye on the surface of the film absorbs infrared radiation. The reaction of the organic dye and the salt, however, produces a mixture of oxidation products and derivatives which have overlapping bands of absorption.

In U.S. Pat. No. 3,104,176 a preformed film of synthetic plastic is immersed in a solution of copper salt, and the copper salts are dispersed on the surface of the film and on the surface of the film pores. The salts produce strictly a surface effect of radiation absorption.

As the prior art filters are films, they require support such as cementing onto glass or other types of lenses. The thinness of the films and thus the number of absorbing ions in the films may limit the absorption characteristics of the filters. Further, since this is an absorption of radiation in a small total volume of film material the resultant buildup of heat by the absorption quickly causes thermal decomposition and destruction of the film.

An important aspect of the present invention is the production of a glass which is used as the filter. The glass may be used directly as lenses for glasses, goggles or the like. Another important aspect of the optical filter of the present invention is to provide high luminous transmittance, that is the transmission of light in the normal optical range visible to the human eye, by means of narrow band absorption characteristics at the frequency doubled Nd-laser which is heart the peak sensitivity of the eye. Another important aspect of the invention is to provide narrow band absorption characteristics in the visible region, so that the filter transmits colors usually easily discernable by the human eye.

It is, therefore, among the objects and advantages of the present invention to form a filter which absorbs radiation from a neodymium laser, both the "doubled" frequency at 530 nm and the primary frequency at 1060 nm.

Another object of the invention is to provide a filter for frequency doubled neodymium lasers which has high visual transmittance.

Another objet of the invention is to provide a filter for frequency doubled neodymium laser light which has narrow band absorption characteristics in the visible region.

A still further object of the invention is to provide a glass, optical filter for frequency doubled neodymium lasers in which a change in the base glass may broaden the absorption band, increase the absorption coefficient or shift the band toward a longer wavelength.

These and other objects and advantages of the invention may be readily ascertained by referring to the following description and the appended drawing in which:

FIG. 1 is a visible region absorption curve of a filter having an equivalent of 45 wt. % erbium oxide in a 3.5mm thick boro-silicate glass.

In general, the invention provides a glass, optical filter having from about 1 to about 75% of a compound providing erbium ($Er^{3+}$) ions, and in certain instances, a compound providing ferrous ($Fe^{2+}$) ions in the glass. In another case, including a compound which produces cupric ($Cu^{2+}$) ions, absorption is additionally at different wavelengths from the erbium and the iron ions. By changing the host glass of the filter, the band width at various absorption peaks may be changed.

For one test, a boro-silicate glass matrix was doped with 45% by weight of erbium oxide, ($Er_2O_3$). This mixture was melted, poured into a mold, and finished to a lens of about 3.5mm thickness. The absorption characteristics of the cooled glass are shown by the curve of FIG. 1. Good absorption is shown by an $Er^{3+}$ peak at 488nm (nanometers) and at 515 and 530 nm by a strong peak of the $Er^{3+}$ band centered at about 520 nm. A change of the base glass provides means for minor adjustment of the shape of the band, increasing the absorption coefficient or shifting the band toward longer wavelenghts. For the present application glass bases such as boro-silicate, phosphate, and lanthanum borate provide an advantage over standard silicate based glasses.

Where the base glass (of ophthalmic quality) has the compound $Er_2O_3$ in a quantity of from 30 to 75%, a filter is produced having optical density of about 3.5 at wavelengths of 530 nm, 515 nm, and 488 nm without causing devitrification of the glass. Borate silicate glasses having 30, 40 and 50 weight pecent of $Er_2O_3$ show similar absorption characteristic curves. Borate silicate glass having 50% $Er_2O_3$ has an optical density of 1 at 530 nm for a 1 mm thickness, and the desired optical density of 3.5 is obtained by increasing the thickness of the glass to 3.5 mm, which is the normal thickness used for safety glasses. Lanthanum borate based glasses containing 30 to 40 wt. % of $Er_2O_3$ show similar absorption curves. The preferred base glass, and the best mode now known for the practice of this invention is described in my copending application Ser. No. 493587 entitled (AO-1885) MULTI-WAVELENGTH OPTICAL FILTER.

Other glass compositions containing the erbium oxide include glasses such as alumino-silicate, barium crown, phosphates, dense flints, soda lime, rubidium crown, and fluoride type glasses. Such glasses may be made with from 30 up to as high as 75 wt: % of erbium oxide. The higher percentages are useful in phosphate glasses, as will be apparent to those skilled in the art.

The broadening of the band at 520 nm is partly a function of the glass composition. The absorption at 530 nm is due either to a weak side band at 533 nm or a broadening of the 520 nm peak, or a combination of the two. Generally a compromise is made between the advantage gained in increased optical density by broadening of these peaks and the disadvantage incurred by the loss of visual transmission due to the broadening of the peaks. Thus, it is possible to easly change the base glass to provide such a compromise.

To provide protection against Nd laser radiation, at a frequency of 1.06 microns, ferrous ($Fe^{2+}$) ions are incorporated in the glass along with the $Er_2O_3$ to absorb light at 1.060 microns. The iron compound may be present in the glass from about 1 to 20 wt. % and may be the ferrous oxide, ferrous chloride, ferrous nitrate, ferrous sulfate, etc.

The filter according to the invention may be fabricated using two different approaches. In the first case, a glass base may be formed with both the $Er^{3+}$ and the $Fe^{2+}$ ions incorporated in the same glass and formed into the lens or shield as the case may be. A second approach is to form separately two lenses, one being a glass base with the $Er^{3+}$ ion and the other being a glass base with the $Fe^{2+}$ ion. These separate glasses are then laminated to provide a single lens which has the effect required of the filter. With a laminated lens, for example, a phosphate base glass containing the iron ion may be laminated with a borate glass containing the erbium ion.

Another modification which may be made in the filter of the invention is the inclusion of cupric copper ($Cu^{2+}$) ion along with the erbium ion. In this case, a phosphate glass containing 4 wt. % of CuO along with 30 wt. % of $Er_2O_3$ provides additional protection at 694 nm and 1060 nm. The copper compound may be used in amounts of from 0.5–10% by weight, and may be various cupric compounds that are ionized in the glass. Such compounds as cupric oxide, chloride, nitrate, bromide, sulfate and the like may be used. Also, three glasses, each with one of the absorbing ions may be laminated in the above manner to form protective eye shields.

What I claim is:

1. An optical filter for laser radiation comprising a base glass containing from 1–75 weight percent of an oxide base of a compound producing $Er^{3+}$ ions and 1–20 weight percent of an iron compound soluble in the glass melt producing $Fe^{2+}$ ions, said ions being uniformly distributed throughout said base glass, and said glass being characterized by high visual transmittance and color transmittance in the human eye range.

2. An optical filter according to claim 1 wherein said compound producing $Er^{+3}$ ions is $Er_2O_3$.

3. An optical filter according to claim 1 wherein said base glass is a lanthanum borate glass.

4. An optical filter according to claim 1 wherein said base glass is a borate silicate glass.

5. An optical filter according to claim 1 wherein said compound having the $Er^{3+}$ ion and the compound having the $Fe^{2+}$ ion are present in a single base glass.

* * * * *

UNITED STATES PATENT OFFICE
CERTIFICATE OF CORRECTION

PATENT NO. : 3,959,171
DATED : May 25, 1976
INVENTOR(S) : Richard F. Woodcock

It is certified that error appears in the above-identified patent and that said Letters Patent are hereby corrected as shown below:

On the last page of the patent, column 4, claim 1, line 14 reading:

"1-75 weight percent of an"

should read:

--1-75 weight percent on an--

Signed and Sealed this

Thirteenth Day of September 1977

[SEAL]

Attest:

RUTH C. MASON
Attesting Officer

LUTRELLE F. PARKER
Acting Commissioner of Patents and Trademarks